United States Patent
Lihl et al.

(10) Patent No.: US 7,547,416 B2
(45) Date of Patent: Jun. 16, 2009

(54) DEWAR VESSEL FOR AUTOMATED CRYOSUBSTITUTION OR LOW-TEMPERATURE SUBSTITUTION, AND APPARATUS FOR AUTOMATED CRYOSUBSTITUTION OR LOW-TEMPERATURE SUBSTITUTION

(75) Inventors: Reinhard Lihl, Vienna (AT); Michael Zimmermann, Leopoldsdorf (AT); Hubert Goll, St. Poelten (AT); Paul Wurzinger, Deutsch-Wagram (AT)

(73) Assignee: Leica Mikrosysteme GmbH, Vienna (AT)

(*) Notice: Subject to any disclaimer, the term of this patent is extended or adjusted under 35 U.S.C. 154(b) by 531 days.

(21) Appl. No.: 11/335,104

(22) Filed: Jan. 19, 2006

(65) Prior Publication Data

US 2006/0162653 A1 Jul. 27, 2006

(30) Foreign Application Priority Data

Jan. 25, 2005 (DE) ........................ 10 2005 003 284

(51) Int. Cl.
*F25B 19/00* (2006.01)
*F25D 13/04* (2006.01)
*B05C 3/00* (2006.01)

(52) U.S. Cl. ............................ 422/102; 62/51.1; 62/65; 118/429

(58) Field of Classification Search ................. 118/429; 62/514 R; 436/176; 422/99
See application file for complete search history.

(56) References Cited

U.S. PATENT DOCUMENTS

| | | | |
|---|---|---|---|
| 3,497,320 A * | 2/1970 | Blackburn et al. ............ 436/44 |
| 4,306,425 A | 12/1981 | Sitte et al. ...................... 62/514 |
| 4,363,783 A | 12/1982 | Sitte .............................. 422/68 |
| 4,422,151 A * | 12/1983 | Gilson ......................... 700/283 |
| 4,723,420 A | 2/1988 | Sitte .............................. 62/514 |
| 5,469,712 A * | 11/1995 | Sitte et al. ..................... 62/51.1 |
| 5,686,313 A | 11/1997 | Sitte et al. .................... 436/176 |
| 5,988,236 A * | 11/1999 | Fawcett ....................... 141/130 |
| 2003/0003577 A1 | 1/2003 | Horstmann .................. 435/395 |
| 2006/0073079 A1* | 4/2006 | Goll et al. ...................... 422/99 |

FOREIGN PATENT DOCUMENTS

| | | |
|---|---|---|
| DE | 29 44 464 | 5/1981 |
| DE | 30 42 578 | 6/1982 |
| DE | 34 25 744 | 1/1986 |
| DE | 38 05 808 | 9/1989 |
| DE | 91 04 344 | 8/1991 |
| DE | 101 59 207 | 6/2003 |
| EP | 0 611 445 | 8/1994 |
| EP | 1 267 164 | 12/2002 |
| WO | 94/05995 | 3/1994 |

OTHER PUBLICATIONS

Leica Mikrosysteme GmbH, Leica EM AFS, Automatic Freeze-Substitution System, Feb. 1997, Vienna, Austria.

* cited by examiner

*Primary Examiner*—Jill Warden
*Assistant Examiner*—Timothy G Kingan
(74) *Attorney, Agent, or Firm*—Simpson & Simpson, PLLC

(57) ABSTRACT

A Dewar vessel (1) for automated cryosubstitution or low-temperature substitution is disclosed. The invention further discloses an apparatus (10) for automated liquid transfer for cryosubstitution or low-temperature substitution. The apparatus (10) encompasses a container (50) that encompasses at least one specimen holder (2) and at least one reservoir holder (20); and wherein a movable transfer container (35) for automated exchange of at least one liquid (42) between the at least one specimen holder (2) and the at least one reservoir holder (20) is provided.

19 Claims, 6 Drawing Sheets

DEWAR VESSEL FOR AUTOMATED CRYOSUBSTITUTION OR LOW-TEMPERATURE SUBSTITUTION, AND APPARATUS FOR AUTOMATED CRYOSUBSTITUTION OR LOW-TEMPERATURE SUBSTITUTION

CROSS REFERENCE TO RELATED APPLICATIONS

This application claims priority of German patent application 10 2005 003 284.2, filed Jan. 25, 2005, which application is incorporated by reference herein.

FIELD OF THE INVENTION

The invention relates to a Dewar vessel for automated cryosubstitution or low-temperature substitution. The invention relates in particular to a Dewar vessel for automated cryosubstitution or low-temperature substitution that is embodied with a neck and is filled with a liquid cooling agent, a chamber for receiving a container being provided in the neck.

The invention further relates to an apparatus for automated cryosubstitution or low-temperature substitution.

BACKGROUND OF THE INVENTION

Patent Application WO 94/05995 discloses an apparatus for the dewatering and/or embedding of preferably frozen specimens. The apparatus encompasses a Dewar vessel filled with liquid nitrogen and a metallic element, anchored at the base of the Dewar vessel, that is made of a material having good thermal conductivity. The metallic element possesses at its upper end, in the Dewar neck attachment region, a cover having a metallic cooling surface. Provided in the Dewar neck is a substitution (PLT) container in which the transfer of liquids for low-temperature substitution is performed manually.

The brochure for the Leica EM AFS discloses a unit according to the existing art. A Dewar vessel is filled with liquid nitrogen, the Dewar neck comprising a chamber or a container that can be brought to a specific temperature. The temperature range extends from −140° C. to +65° C. The desired temperature is set via a control loop and built-in heating elements. Here as well, liquid exchange must be accomplished manually.

German Utility Model DE 91 04 344.1 discloses a cooling device for specimen preparation for an electron microscope. The cooling device encompasses a holding insert that is subdivided into at least two segments. Both segments are equipped with orifices, of which the orifices in one segment serve to retain a container for the specimens to be freeze-dried. Reservoir vessels having reagents are retained in the orifices of the other segment. The specimens and the reagents are thereby cooled to the required working temperature. An automatic transfer of the reagents from one region of the container into the next is not disclosed.

SUMMARY OF THE INVENTION

The object of the present invention is therefore to create a Dewar vessel that makes possible the automation of manual activities in the context of cryosubstitution or low-temperature substitution.

Another object is, by way of the invention, to make possible a transfer of cold substitution media (solvents) and/or embedding media (synthetic resins), to enhance accuracy in the preparation of mixtures, and to reduce contamination susceptibility.

The above object is achieved by an apparatus for cryosubstitution or low-temperature substitution that encompasses: a neck wherein the Dewar vessel is filled with a liquid cooling agent, a chamber formed in the neck for receiving a container wherein the chamber encompasses at least one specimen holder and at least one reservoir holder; and an apparatus for automated exchange of at least one liquid between the at least one specimen holder and the at least one reservoir holder is provided.

A further object of the invention is to create an apparatus for automated cryosubstitution or low-temperature substitution with which a transfer of cold substitution media (solvents) and/or embedding media (synthetic resins) is made possible, accuracy in the preparation of mixtures is enhanced, and contamination susceptibility is reduced.

The above object is achieved by an apparatus for cryosubstitution or low-temperature substitution that encompasses: a container that encompasses at least one specimen holder and at least one reservoir holder; and a movable transfer container for automated exchange of at least one liquid between the at least one specimen holder and the at least one reservoir holder.

It is advantageous if the Dewar vessel for automated cryosubstitution or low-temperature substitution is embodied with a neck and is filled with a liquid cooling agent. A chamber for receiving a container is provided in the neck, the container encompassing at least one specimen holder and at least one reservoir holder. Also provided is an apparatus for automated exchange of at least one liquid between the at least one specimen holder and the at least one reservoir holder.

An apparatus for automated cryosubstitution or low-temperature substitution is likewise advantageous if a container is provided that encompasses at least one specimen holder and at least one reservoir holder; and wherein a movable transfer container for automated exchange of at least one liquid between the at least one specimen holder and the at least one reservoir holder is provided.

The apparatus can be immovably joined to the Dewar vessel. The apparatus can likewise be embodied removably from the Dewar vessel.

The apparatus encompasses a movable transfer container that transports the liquid between the at least one specimen holder and the at least one reservoir holder. The transfer container can be a syringe or a pipette. The liquid is taken into or ejected from the transfer container in motorized, pneumatic, or hydraulic fashion.

The apparatus for automated exchange of at least one liquid between the at least one specimen holder and the at least one reservoir holder performs the liquid transfer in remotely controlled fashion between the at least one reservoir holder and the at least one specimen holder. The transfer container moves correspondingly back and forth, thus enabling the liquid transfer.

An electronic control system or a computer software program is provided which makes possible programming of a chronological sequence of transfer steps between the at least one reservoir holder and at least one specimen holder.

The container is embodied as a cup open at the top, the specimen holders and reservoir holders being arranged in the container on a circle about a central axis of the apparatus. The apparatus can furthermore have integrated into it one or more UV light-emitting diodes (LEDs) that polymerize embedding material (synthetic resin) for the specimen.

BRIEF DESCRIPTION OF THE DRAWINGS

Further advantages and advantageous embodiments of the invention may be inferred from the dependent claims and are the subject matter of the Figures below and the descriptions thereof.

In the individual drawings.

DETAILED DESCRIPTION OF THE INVENTION

Figure 1:
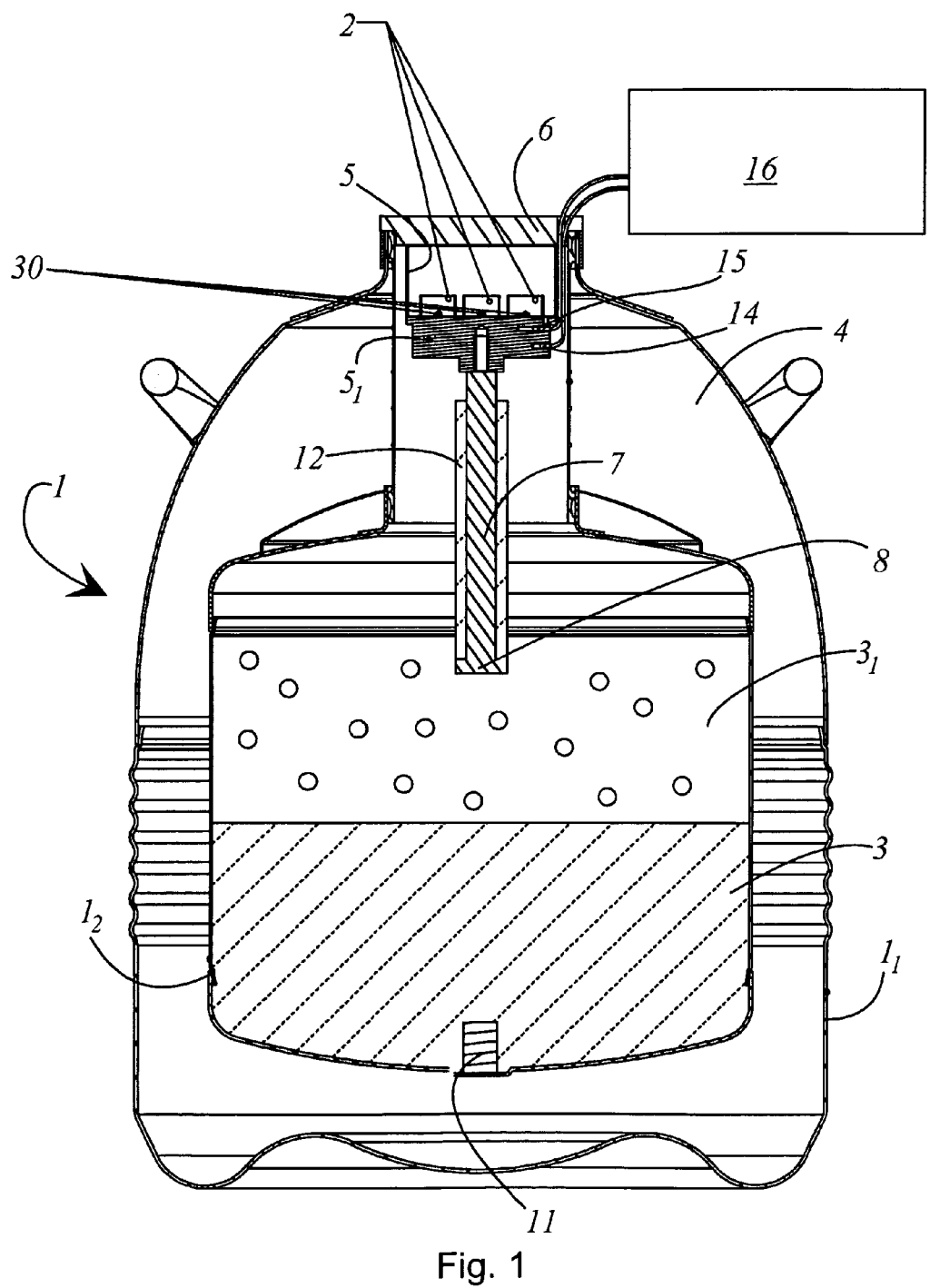
FIG. 1 is a cross section through a Dewar vessel for cryosubstitution or low-temperature substitution.

FIG. 1 is a cross section through one possible embodiment of a Dewar vessel 1 for cryosubstitution or low-temperature substitution. In the description that follows, identical reference characters are used for identical elements. The cooling apparatus shown in FIG. 1 serves for cryosubstitution or low-temperature substitution of biological and/or other water-containing specimens. The Dewar vessel encompasses an inner container $1_2$ and an outer container $1_1$. The inner container is filled with a liquid cooling agent that is preferably liquid nitrogen 3. A chamber 5 is inserted into neck $1_3$ of Dewar vessel 1. Chamber 5 is cup-shaped and possesses a heavy base $5_1$. Chamber 5 is open at the top and can be closed off with a cover 6 for insulation with respect to ambient temperature. Chamber 5 serves to receive multiple specimen holders 2 in which specimens 30 for cryosubstitution or low-temperature substitution are located. A first thermal conduction rod 7 is joined to base $5_1$ of chamber 5. A platform 8 is provided at the end of first thermal conduction rod 7 facing away from base $5_1$ of chamber 5. Platform 8 can be detachably joined to first thermal conduction rod 7. It is also conceivable for first thermal conduction rod 7 and platform 8 to be embodied integrally. Above platform 8, first thermal conduction rod 7 is surrounded by an insulator 12. Insulator 12 serves to insulate first thermal conduction rod 7 with respect to liquid nitrogen 3 or cold nitrogen gas $3_1$. Insulator 12 causes the heat flux that cools chamber 5 or base $5_1$ to be directed principally via platform 8. The cooling power can therefore advantageously be determined by modifying the geometrical dimensions or selecting a suitable material for first thermal conduction rod 7. The temperature in chamber 5 can be regulated by operating at least one heating element 14. Also provided is at least one temperature sensor 15 that is used for temperature measurement. Temperature sensor 15 can be embodied as a thermocouple or a resistance temperature sensor. The temperature signal is used as feedback for an electronic regulating system 16 that controls the temperature of chamber 5 by adapting the heating output of heating element 14. The length of first thermal conduction rod 7 is advantageously selected in such a way that platform 8 is immersed in liquid nitrogen 3 only when a certain fill level is reached. With a high fill level, platform 8 is immersed in liquid nitrogen 3, and chamber 5 is coupled via first thermal conduction rod 7 directly to liquid nitrogen 3. With a low fill level, platform 8 interacts with cold nitrogen gas $3_1$. Cold nitrogen gas $3_1$ is heated by the heat flux from chamber 5 into inner container $1_2$ of Dewar vessel 1. By convection and by interaction with the walls of inner container $1_2$, this heat is fed back into liquid nitrogen 3 and causes an increase in the evaporation rate. The result is that platform 8 and chamber 5 arrive at an equilibrium temperature that is largely independent of the present fill level of liquid nitrogen 3 in inner container $1_2$. It is self-evident that the thermal coupling between chamber 5 and liquid nitrogen 3 is much greater at a high fill level than at a low fill level. Lower temperatures in chamber 5 can therefore be attained with a high fill level. On the other hand, the consumption of liquid nitrogen is lower with a low fill level.

This arrangement is advantageous in that in standard substitution processes, the lowest process temperatures (−90° C. and below) are needed at the beginning of the processes. The temperature is raised in the course of the substitution processes. Because liquid nitrogen 3 is also consumed during the process, the cooling power achievable by way of first thermal conduction rod 7 and platform 8 reflects the temperature profile of the substitution process. At the same time, insulator 12 also limits the coupling to liquid nitrogen 3 when the fill level is high. High temperatures can therefore be set even in this situation, with no need to exceed reasonable limits for nitrogen consumption and for the requisite heating output of heating element 14.

Figure 2:
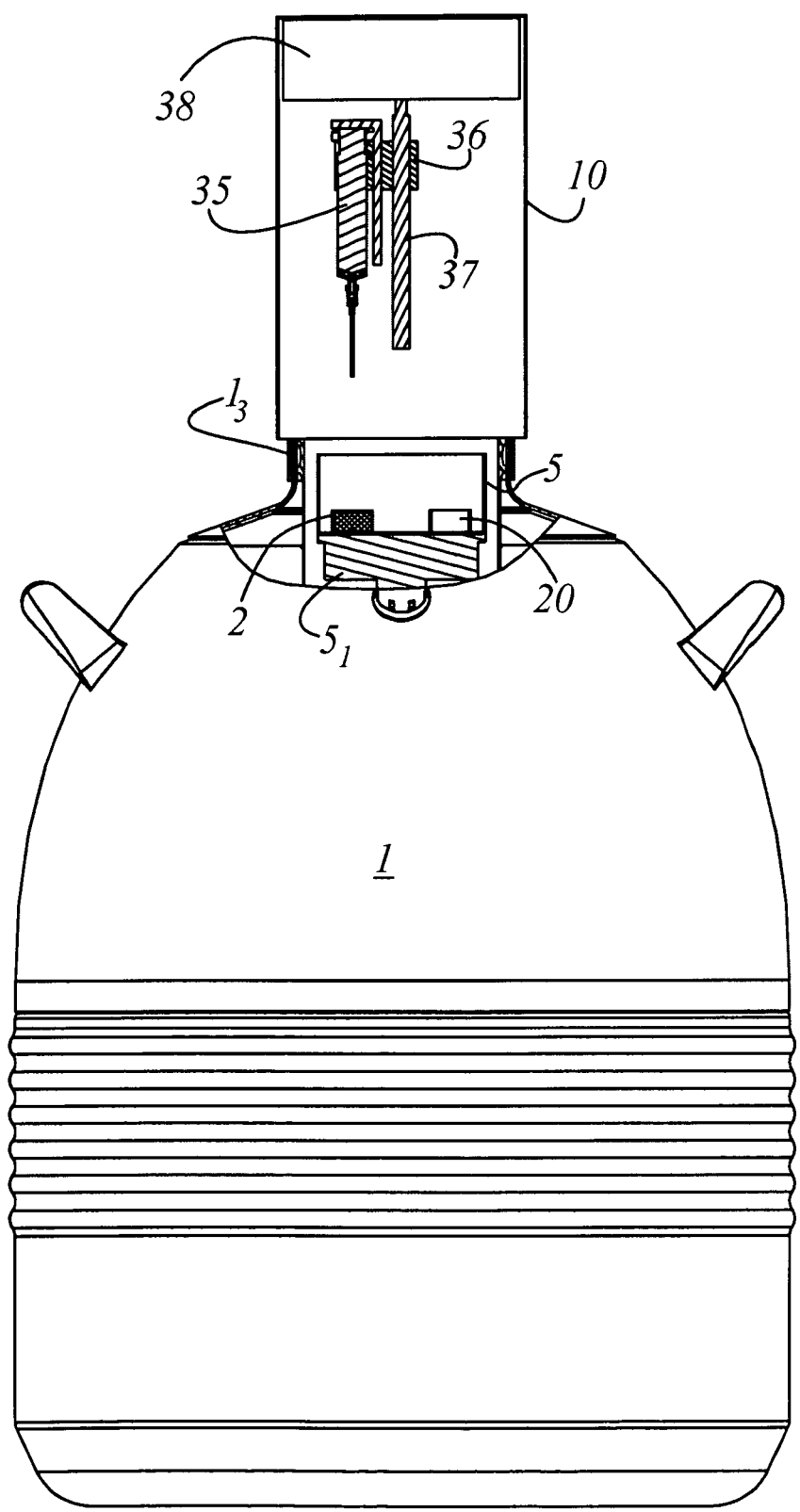
FIG. 2 schematically depicts a Dewar vessel onto which the apparatus for liquid transfer for automated cryosubstitution or low-temperature substitution is placed.

FIG. 2 schematically depicts a Dewar vessel 1 onto which apparatus 10 for automated liquid transfer for cryosubstitution or low-temperature substitution is placed. A chamber 5 is inserted into neck $1_3$ of Dewar vessel 1. Chamber 5 is cup-shaped and possesses a heavy base $5_1$. Chamber 5 is open at the top. Chamber 5 serves to receive a container 50 that encompasses at least one specimen holder 2 and at least one reservoir holder 20. It is also conceivable for the at least one specimen holder 2 and the at least one reservoir holder 20 to be inserted directly into the chamber if the latter is embodied to be cup-shaped and open at the top. A movable transfer container 35 is provided for automated exchange of at least one liquid between the at least one specimen holder 2 and the at least one reservoir holder 20. Apparatus 10 can be immovably joined to Dewar vessel 1. It is also conceivable for apparatus 10 to be embodied removably from Dewar vessel 1. Apparatus 10 is embodied, for example, as a module that can be placed as necessary, for example by the user, onto a Dewar vessel 1. Transfer container 35 is a syringe or a pipette. The liquid is taken into or ejected from transfer container 35 in motorized, pneumatic, or hydraulic fashion. Apparatus 10 is equipped for that purpose with an actuation element 36 with which motorized, pneumatic, or hydraulic intake or ejection of the liquid into or from transfer container 35 is accomplished. A control unit 38 is provided with which apparatus 10 performs the automated transfer of at least one liquid between the at least one specimen holder 2 and the at least one reservoir holder 20 in remotely controlled fashion. Transfer container 35 moves correspondingly back and forth, thus enabling the liquid transfer. Transfer container 35 can move up and down along an axis 37. Control unit 38 is what makes possible programming of a chronological sequence of transfer steps between the at least one reservoir holder 20 and the at least one specimen holder 2.

Figure 3:
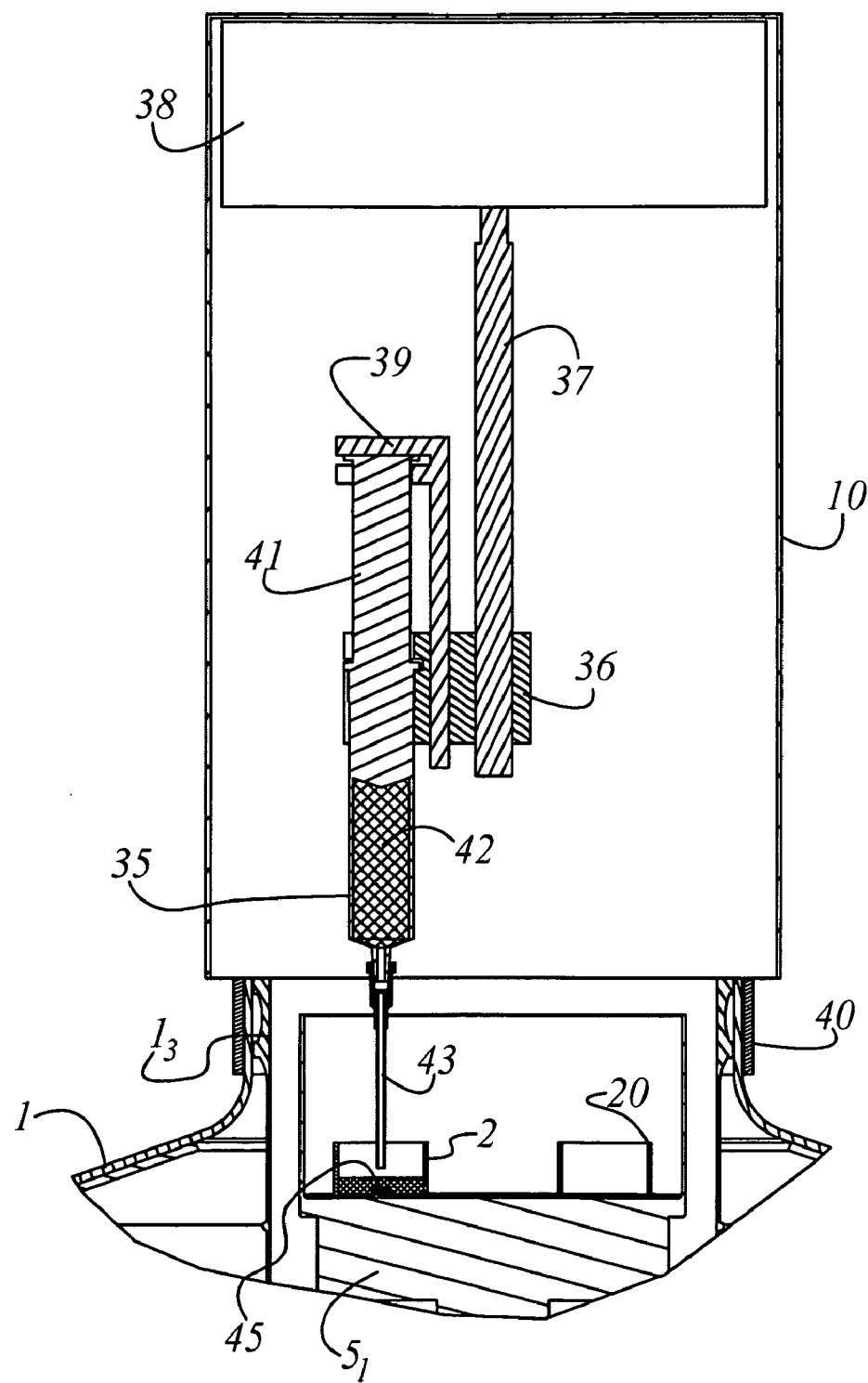
FIG. 3 is an enlarged depiction of a first embodiment of the apparatus for liquid transfer for automated cryosubstitution or low-temperature substitution.

FIG. 3 is an enlarged depiction of a first embodiment of apparatus 10 for automated cryosubstitution or low-temperature substitution. Apparatus 10 can be placed onto neck $1_3$ of Dewar vessel 1. Apparatus 10 is embodied for that purpose with a flange 40 that fits around neck $1_3$ of Dewar vessel 1. It is also conceivable for the apparatus to be coupled to neck $1_3$ of Dewar vessel 1 via mechanical coupling elements, e.g., a bayonet. Transfer container 35 can be moved up and down along axis 37. The chronological sequence of transfer steps between the at least one reservoir holder 20 and the at least one specimen holder 2 is accomplished in co-action with actuation element 36 and control unit 38. A plunger 41 of transfer container 35, which makes possible the intake or ejection of liquid 42, is likewise actuated by means of actuation element 36. In the embodiment depicted here, transfer container 35 is equipped with a hollow needle 43 that makes possible accurate introduction and/or removal of liquid 42 into and/or out of specimen holder 2 and/or transfer container 35. A specimen 45 for cryosubstitution or low-temperature substitution is placed in specimen holder 2.

Figure 4:
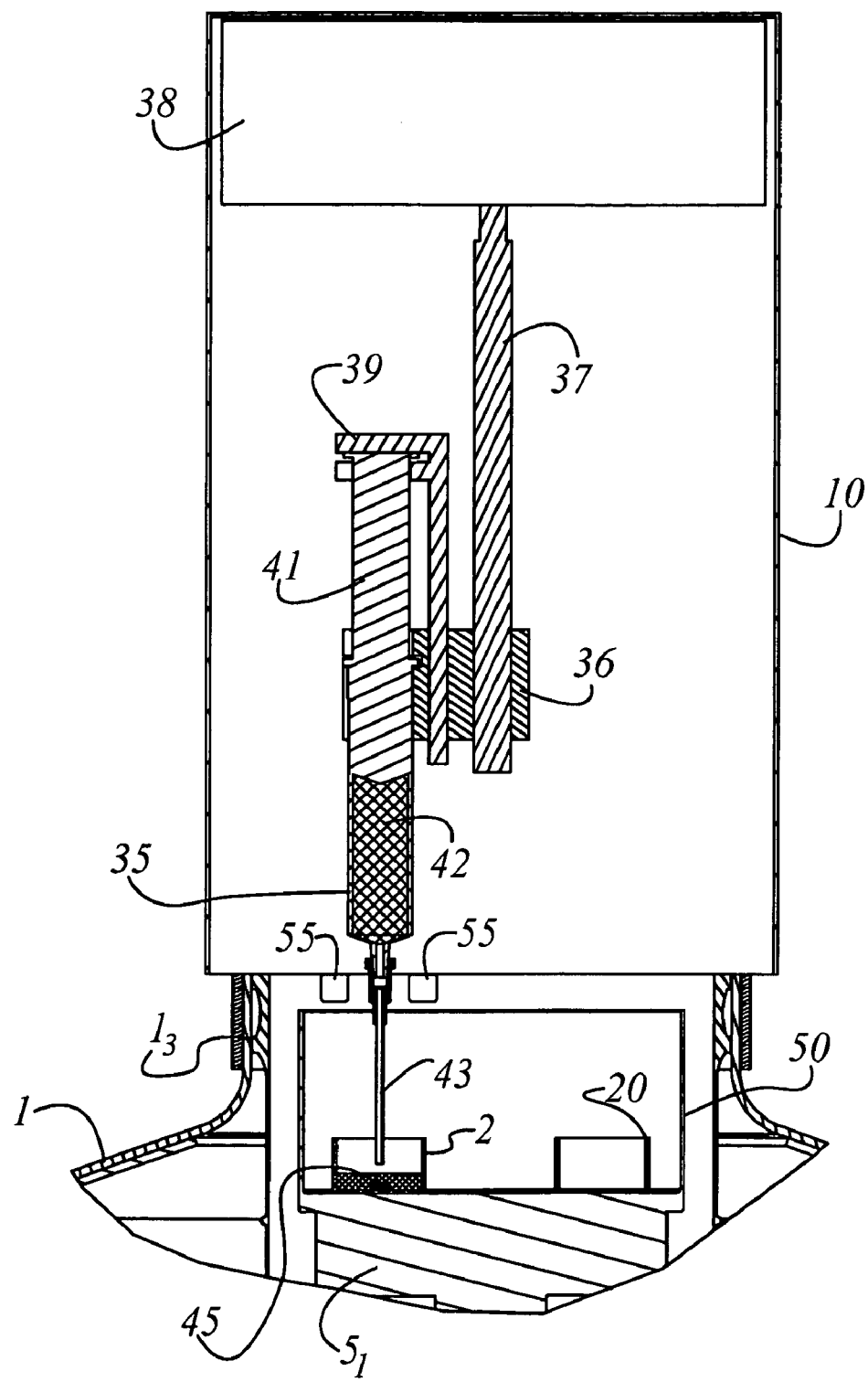
FIG. 4 is an enlarged depiction of a second embodiment of the apparatus for liquid transfer for automated cryosubstitution or low-temperature substitution; and, FIG. 5 is a perspective view of the container for receiving at least one specimen holder and at least one reservoir holder.

FIG. 4 is an enlarged depiction of a second embodiment of apparatus 10 for automated cryosubstitution or low-temperature substitution. The difference as compared with the embodiment depicted in FIG. 3 is that apparatus 10 for automated cryosubstitution or low-temperature substitution has integrated into it at least one UV diode 55 that polymerizes a liquid 42 serving as embedding material for specimen 45.

Figure 5:
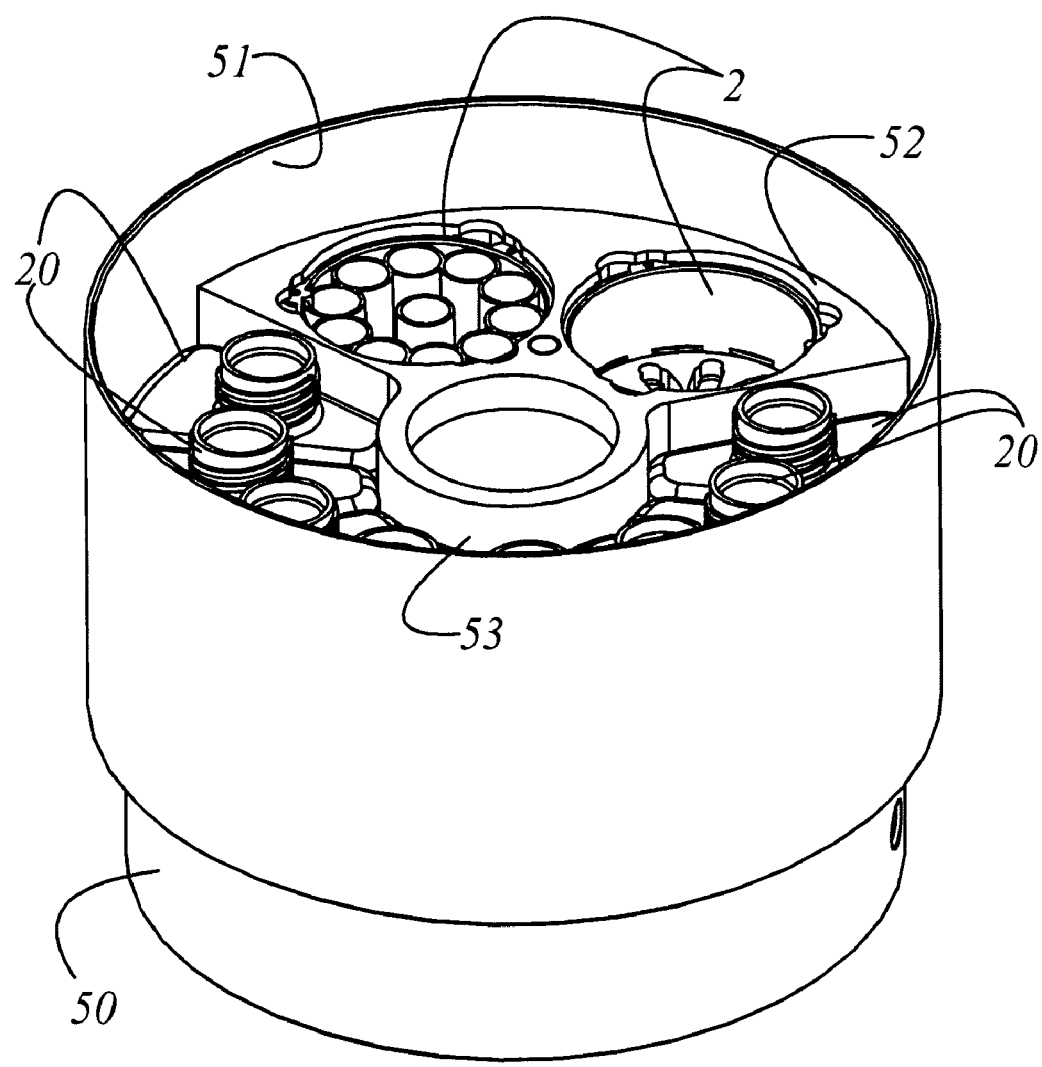

FIG. 5 is a perspective view of container 50 for receiving at least one specimen holder 2 and at least one reservoir holder 20. According to the embodiment depicted here, container 50 is embodied as a cup 51 open at the top. Container 50 is subdivided into a first sector 52 and a second sector 53. Specimen holders 2 are provided in first sector 52. Reservoir holders 20 are provided in second sector 53. Specimen holders 2 are suitable for receiving different types of specimen containers. Reservoir holders 20 are embodied as bottles and are inserted into second sector 53. Second sector 53 has the shape of an annulus sector, so that each of reservoir holders 20 likewise possesses the shape of an annulus sector.

Figure 6:
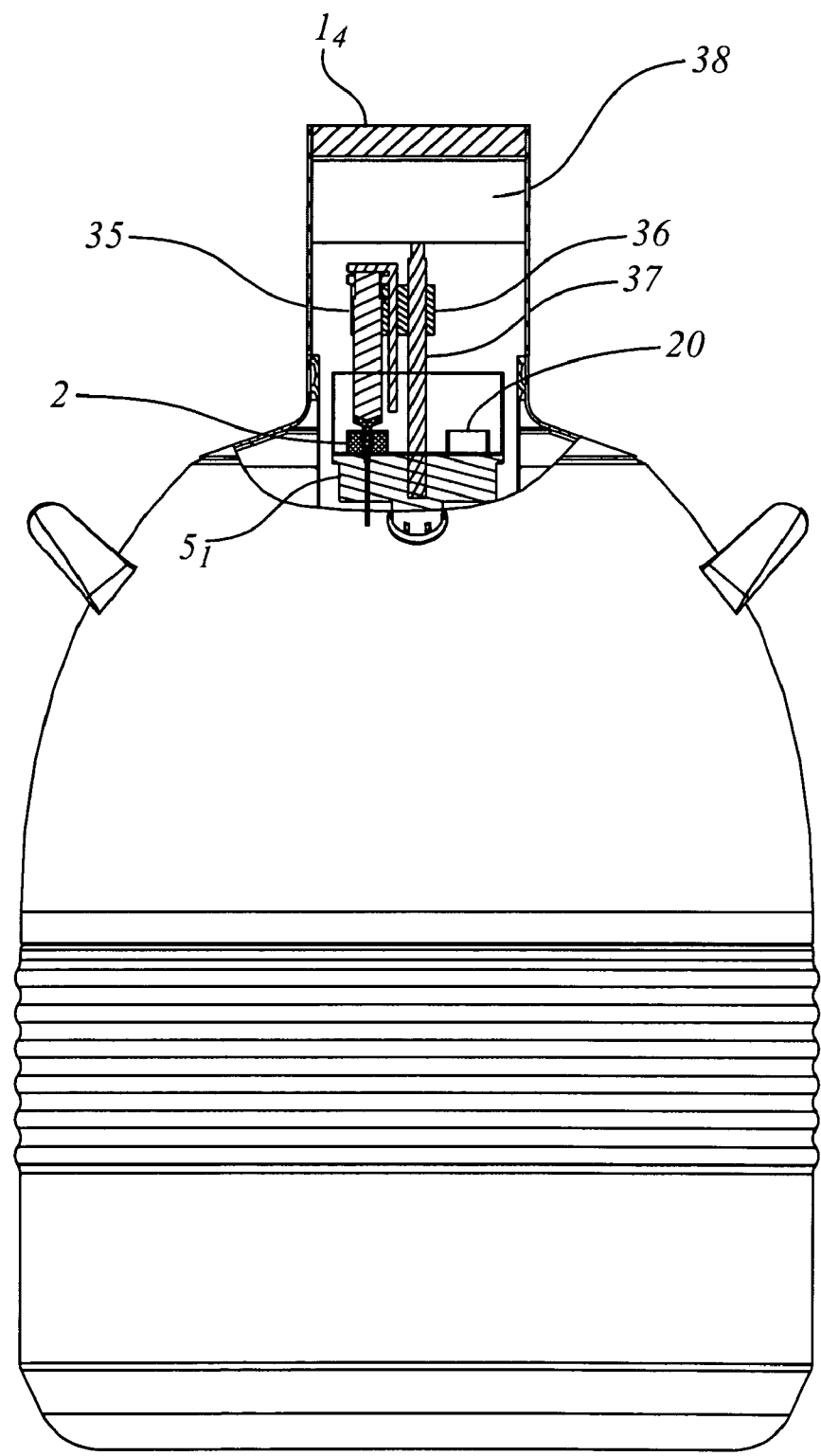
FIG. 6 schematically depicts an embodiment in which the apparatus for liquid transfer is contained within the neck of the Dewar vessel.

FIG. 6 is a side view of an alternate embodiment of the present invention. In this embodiment, chamber 5 is inserted into the neck $1_3$ of Dewar vessel 1. Movable transfer container 35 is positioned within neck 5 of vessel 1 to provide for automated exchange of at least one liquid between the at least one specimen holder 2 and the at least one reservoir holder 20 within neck 5 of vessel 1 and is covered by cover $1_4$. As described above, transfer container 35 may be a syringe or a pipette. The liquid is taken into or ejected from transfer container 35 in motorized, pneumatic, or hydraulic fashion. Actuation element 36 with which motorized, pneumatic, or hydraulic intake or ejection of the liquid into or from transfer container 35 is contained under cover $1_4$ with transfer container 35. Control unit 38 is provided to perform the automated transfer of at least one liquid between the at least one specimen holder 2 and the at least one reservoir holder 20 in remotely controlled fashion. Transfer container 35 moves correspondingly back and forth within neck 5, thus enabling the liquid transfer. Transfer container 35 can move up and down along an axis 37. Control unit 38 is what makes possible programming of a chronological sequence of transfer steps between the at least one reservoir holder 20 and the at least one specimen holder 2.

What is claimed is:

1. A Dewar vessel for automated cryosubstitution or low-temperature substitution comprising: a neck wherein the Dewar vessel is filled with a liquid cooling agent, a chamber formed in the neck for receiving a container wherein the chamber encompasses at least one specimen holder and at least one reservoir holder and a movable transfer container for automated exchange of at least one liquid between the at least one specimen holder and the at least one reservoir holder wherein the movable transfer container is a syringe or a pipette; and,
wherein the liquid is taken into or ejected from the movable transfer container in a motorized, pneumatic or hydraulic fashion.

2. The Dewar vessel according to claim 1, wherein the apparatus is immovably attached to the Dewar vessel.

3. The Dewar vessel according to claim 1, wherein the apparatus is embodied removably from the Dewar vessel.

4. The Dewar vessel according to claim 1, wherein the quantity of liquid to be taken in or ejected is settable in steps or continuously.

5. The Dewar vessel according to claim 1, wherein the apparatus for automated exchanged of at lease one liquid between the at least one specimen holder and the at least one reservoir holder functions in remotely controlled fashion, the transfer container moving correspondingly back and forth and thus enabling the liquid transfer.

6. The Dewar vessel according claim 5, wherein an electronic control system or a computer software program is provided which makes possible programming of a chronological sequence of transfer steps between the at least one reservoir holder and at least one specimen holder.

7. The Dewar vessel according to claim 1, wherein the container is embodied as a cup open at the top; and wherein the specimen holders and reservoir holders are arranged in the container on a circle about a central axis of the apparatus.

8. The Dewar vessel according to claim 1, wherein the apparatus has integrated into it at least one UV diode that polymerizes embedding material for the specimen.

9. The Dewar vessel according to claim 1, wherein the chamber is embodied with a heavy base; wherein the heavy base of the chamber is joined to a thermal conduction rod that is mounted, at the end facing away from the base, to a platform; and the thermal conduction rod is equipped, above the platform, with an insulator.

10. The Dewar vessel according to claim 1, wherein the liquid cooling agent is liquid nitrogen.

11. The Dewar vessel according claim 9, wherein at least one heating element and at least one temperature sensor are recessed into the base of the chamber; and the heating element and temperature sensor is connected to an electronic regulating system.

12. The Dewar vessel according to claim 9, wherein a further heating element that preferably is electrically operated is immersed into the liquid nitrogen, in order additionally to evaporate liquid nitrogen during operation so that the cold gas cools the platform of the first cooling rod.

13. The Dewar vessel according to claim 1, wherein at least one sensor is provided that ascertains the fill level of the liquid nitrogen in the Dewar vessel.

14. An apparatus for automated cryosubstitution or low-temperature substitution, comprising: a container that encompasses at least one specimen holder and at least one reservoir holder and a movable transfer container for automated exchange of at least one liquid between the at least one specimen holder and the at least one reservoir holder;
wherein the movable transfer container is a syringe or a pipette; and,
wherein the liquid is taken into or ejected from the movable transfer container in a motorized, pneumatic or hydraulic fashion.

15. The Dewar vessel according to claim 14, wherein the quantity of liquid to be taken in or ejected is settable in steps or continuously.

16. The apparatus according to claim 14, wherein the movable transfer container is remotely controlled, so that an automated exchange of at least one liquid between the at least one specimen holder and the at least one reservoir holder is accomplished, the transfer container moving correspondingly back and forth and thus enabling the liquid transfer.

17. The apparatus according to claim 14, wherein an electronic control system or a computer software program is provided which makes possible programming of a chronological sequence of transfer steps between the at least one reservoir holder and the at least one specimen holder.

18. The apparatus according to claim 14, wherein the container is embodied as a cup open at the top; wherein the specimen holders and reservoir holders are arranged in the container on a circle about a central axis of the apparatus.

19. The apparatus according to claim 14, wherein at least one UV diode that polymerizes embedding material for the specimen is integrated into the apparatus.

* * * * *